United States Patent [19]

Batchelor et al.

[11] Patent Number: 4,791,136
[45] Date of Patent: Dec. 13, 1988

[54] PHARMACOLOGICALLY ACTIVE KETONES AND USE

[75] Inventors: John F. Batchelor, Beckenham; Richard M. Hyde, Croydon; David J. Livingstone, Beckenham, all of England

[73] Assignee: Burroughs Wellcome Co., Research Triangle Park, N.C.

[21] Appl. No.: 891,768

[22] Filed: Jul. 30, 1986

Related U.S. Application Data

[62] Division of Ser. No. 662,709, Oct. 19, 1984, Pat. No. 4,626,431.

[30] Foreign Application Priority Data

Oct. 25, 1983 [GB] United Kingdom ............... 8328495

[51] Int. Cl.[4] .................................................. A61K 31/35
[52] U.S. Cl. .................................................... 514/456
[58] Field of Search ....................................... 514/456

[56] References Cited

U.S. PATENT DOCUMENTS

| | | | |
|---|---|---|---|
| 3,706,768 | 12/1972 | Bays | 549/393 |
| 3,755,319 | 8/1973 | Bays | 544/109 |
| 4,591,600 | 5/1986 | Creuzet et al. | 514/456 |

FOREIGN PATENT DOCUMENTS 1312620 4/1973 United Kingdom .

OTHER PUBLICATIONS

Assem et al., British Medical Journal, 1974, 2, 93–95.
Chemical Abstracts 81:33553h (1974).
Pfister et al., Journal of Medicinal Chemistry, 1972, 15, 10, 1032–1035.

Primary Examiner—Albert T. Meyers
Assistant Examiner—John M. Kilcoyne
Attorney, Agent, or Firm—Donald Brown

[57] ABSTRACT

Use of compounds of formula (I)

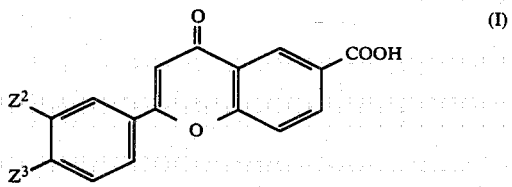

to provide a more effective delivery of oxygen to the tissues of a mammalian, including human, recipient.

In vivo applications include the relief or amelioration of conditions wherein there is tissue hypoxia; in vitro the compounds are of use in the storage of mammalian, including human, red blood cells to maintain their oxygen-delivery capacity and prolong their useful storage life.

Also provided is a sterile, sealed vessel containing an anticoagulant, a non-toxic amount of a compound of formula (I) and optionally mammalian, in particular human, red blood cells.

12 Claims, No Drawings

PHARMACOLOGICALLY ACTIVE KETONES AND USE

This is a division of application Ser. No. 662,709 filed Oct. 19, 1984 now U.S. Pat. No. 4,626,431.

This invention relates to ketones useful in medicine, to pharmaceutical formulations and other presentation forms containing such compounds and the preparation thereof, and to the use of the compounds in medicine.

The present invention more particularly relates to the ketones of formula (I)

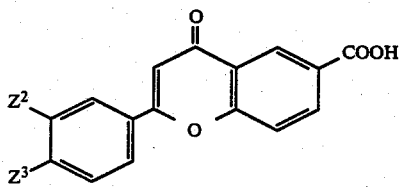

as hereinafter defined, together with pharmacologically acceptable salts thereof, which have been described in the literature as antiallergic agents able to inhibit release of spasmogens from antigen-antibody reactions such as occur in the rat during the passive cutaneous anaphylaxis (PCA) test; see for example *Eur. J. Med. Chem-Chimica Therapeutica*, 13, 33 (1978).

It has now surprisingly been found that the said compounds enable an increase in oxygen liberation from oxyhaemoglobin and are thus of value in both human and veterinary medicine in a field entirely unrelated to and distinct from that suggested by their previously taught activity.

Human haemoglobins are composed of four polypeptide (globin) chains which together comprise the haemoglobin tetramer; each chain surrounds a porphyrin molecule (heam) containing a central iron atom to which oxygen is reversibly bound. When a graph is plotted of the percentage saturation of haemoglobin with oxygen (ordinate) against the partial pressure of oxygen, sometimes called the oxygen tension (abscissa) a characteristic sigmoid curve is obtained, the oxygen-dissociation curve. A displacement of the curve to the *left* of the "normal" position would indicate an increase in the affinity for oxygen of the haemoglobin, a lower oxygen tension then being required to produce a given percentage saturation, while conversely a displacement to the *right* would indicate a reduced oxygen affinity and hence a requirement for a higher oxygen tension for a given percentage saturation. It follows that upon displacement of the curve to the right there is a reduction in the percentage of oxyhaemoglobin present at any given oxygen tension and hence an increased liberation of oxygen upon a fall in tension to any given level.

The compounds of formula (I) as hereinafter defined, induce an in vitro right-displacement of the oxygen-dissociation curve (a) of fresh whole human blood, and (b) of whole human blood subjected to a procedure (incubation overnight at 37° C.) producing changes similar to those seen in blood stored for extended periods by transfusion services and the like (vide infra).

The compounds thus have applications both in vivo and in vitro in circumstances where it is desirable to provide a more effective delivery of oxygen to the tissues of the (eventual) recipient.

In vivo applications for the compounds include the following, many of which may be together classed as the relief or amelioration of conditions wherein the delivery of oxygen to the tissues is impaired, i.e. wherein there is tissue hypoxia:

the treatment of shock the treatment of cardiac ischaemia, for example after myocardial infarction (coronary thrombosis), and the relief of sequelae thereto such as angina pectoris the treatment of cerebral ischaemia and of cerebrovascular accidents in general the relief of intermittent claudication the treatment of placental insufficiency in gravid females the treatment of certain anaemic conditions and in particular pathological anaemia in preterm infants the treatment of the microvascular complications of diabetes mellitus the treatment of hypovolaemic anaemia of traume (the so-called "missing blood syndrome")

as an adjunct to anaesthesia in cardiac bypass surgery, in particular in patients having compromised respiration applications in which a pathological tissue or invading organism is made more sensitive to treatment by increasing the partial pressure of oxygen in its environment, for example:

the radiosensitization of tumours as an adjunct to deep X-ray therapy, with or without concomitant hyperbaric oxygen treatment the treatment of infections of oxygen-sensitive parasites, for example anaerobic bacteria.

A major in vitro application for the compounds is in the field of blood storage. As is well known there is an ever-present need for human blood by medical services throughout the world for use in a wide variety of live-supportive measures. For the majority or recipients whole blood is the only acceptable material as although a number of alternatives have been proposed, none has been found to be a completely satisfactory substitute. The collection, storage and distribution of blood is generally catered for by specialist transfusion services or "blood banks" as exemplified by the National Blood Transfusion Service in the United Kingdom. The effective and economic operation of such agencies is however in large measure governed by the fact that whole blood or, more correctly, the red blood cells (erythrocytes) therein, even when stored as customarily at 4° C., have a very limited "shelf-life" generally accepted as 21 days after removal from the donor. By the end of this period they are considered unsuitable for transfusion and are discarded and there has been considerable research into methods for prolonging the useful life of stored red blood cells and thus reducing the wastage due to "out-dating".

A particular feature of the ageing of red blood cells during storage is a progressive left-displacement of the oxygen-dissociation curve associated with a fall in intracellular levels of 2,3-diphosphoglycerate (DPG), the erythrocytes' natural right-displacement effector. As previously indicated a left-displacement is associated with the haemoglobin having an increased affinity for oxygen and hence ageing cells exhibit a progressive decline in their ability to deliver oxygen to the peripheral tissues following transfusion. Although this property is gradually restored within the recipient's body as DPG levels recover, the initial deficiency is of literally vital significance as the prime reason for transfusing red blood cells (as distinct from just plasma) is generally the immediate prevention or reversal of tissue hypoxia (vide supra). The present compound, in displacing the oxygen-dissociation curve to the right, are of value not only in maintaining the oxygen-delivery capacity of stored red blood cells, thus improving their quality and providing improved oxygen-delivery in the immediate post-transfusion period, but also in prolonging their useful storage life.

In formula (I) as set forth above, one of $Z^2$ and $Z^3$ is selected from hydroxyl and a group $-O(C_nH_{2n})X$ where X is selected from hydrogen and hydroxyl and
n is an integer from 1 to 3,

*provided that* when X is hydroxyl *then* n is always greater than 1 *and* no single carbon atom in the radical $-(C_nH_{2n})-$ is attached to both oxygen atoms and
the other of $Z^2$ and $Z^3$ is hydrogen
together with pharmacologically acceptable salts thereof.

When n is 3 the moiety $-(C_nH_{2n})-$ can be linear or branched.

In the salts of the compounds of formula (I) the biological activity resides in the anionic moiety and the identity of the cation is of less importance although for use in medicine it should be pharmacologically acceptable to the eventual recipient. Suitable salts include ammonium salts, alkali metal salts such as sodium and potassium salts, alkaline earth salts such as magnesium and calcium salts, and salts formed with organic bases, for example, amine salts derived from mono-, di- or tri(lower alkyl) or (lower alkanol)amines such as triethanolamine and diethylaminoethylamine, and salts with heterocyclic amines such as piperidine, pyridine, piperazine and morpholine.

A particularly preferred compound of formula (I) is 3'-methoxyflavone-6-carboxylic acid, together with pharmacologically acceptable salts thereof.

Other compounds of formula (I) include
3'-hydroxyflavone-6-carboxylic acid
4'-hydroxyflavone-6-carboxylic acid
3'-(2-hydroxyethoxy)flavone-6-carboxylic acid, m.pt. (sodium salt, hemihydrate)
4'-(2-hydroxyethoxy)flavone-6-carboxylic acid, m.pt. (sodium salt, 2.5 hydrate) above 360° C.

together with pharmacologically acceptable salts thereof.

The compounds of formula (I) and their salts may be prepared by methods known in the art and in this regard reference is made, by way of illustration only, to the above-referenced literature and to the following standard texts (i) "*Protective Groups in Organic Chemistry*" ed. J. F. W. McOmie, Plenum Press (1973), ISBN 0-306-30717-0;

(ii) "*Compendium of Organic Synthetic Methods*" ed. I. T. Harrison and S. Harrison, Wiley-Interscience, Vol. I (1971) ISBN 0-471-35550-X, Vol. II (1974) ISBN 0-471-35551-8 and Vol. III (ed. L. S. Hegedus and L. Wade) (1977) ISBN 0-471-36752-4; and (iii) Rodd's "*Chemistry of Carbon Compounds*" second edition, Elsevier Publishing Company.

All references identified hereinabove or in the following are hereby incorporated herein by reference thereto.

The compounds of formula (I) as above defined, may be used in both human and veterinary medicine in circumstances such as those previously identified where it is desirable to provide a more effective delivery of oxygen to the tissues of the (eventual) recipient. When administered in vivo the compounds may be used both on a regular maintenance basis and for the relief or amelioration of acute crisis states.

For in vivo use the compounds may be administered to the human or non-human recipient by a route selected from oral, parenteral (including subcutaneous, intradermal, intramuscular and intravenous) and rectal. The size of an effective dose of a compound will depend upon a number of factors including the identity of the recipient, the precise conditionto be treated and its severity and the route of administration and will ultimately be at the discretion of the attendant physician or veterinarian. An effective dose will generally be in the range 1 to 500 mg/kg bodyweight of recipient per day, more generally in the range 10 to 250 mg/kg bodyweight per day and most often in the range 25 to 100 mg/kg bodyweight per day, a particularly suitable dose being 50 mg/kg bodyweight per day (all doses calculated as the carboxyl acid of formula (I); for salts the figures would be adjusted proportionately). The desired dose is preferably presented as between two and four sub-doses administered at appropriate intervals throughout the day. Thus where two sub-doses are employed each will generally be in the range 0.5 to 250, more generally 5 to 125 and most often 12.5 to 50 mg (acid)/kg bodyweight with an optimum of 25 mg (acid)/kg bodyweight.

A daily dose for a human being weighing of the order of 50 kg will thus generally be in the range 50 mg to 25 g (acid), more generally in the range 500 mg to 12.5 g (acid) and most often in the range 1.25 g to 5 g (acid) and may be conveniently presented as two equal unit sub-doses of 25 mg to 12.5 g (acid), more generally 250 mg to 6.25 g (acid) and most often 0.625 g to 2.5 g (acid). Optimally a human daily dose is 2.5 g (acid) coneniently presented as two unit sub-doses each of 1.25 g (acid). For veterinary use, for example in the treatment of non-human mammals such as cats, dogs, cattle, sheep, pigs and horses, the above-recited doses would be increased or decreased at the discretion of the veterinarian having regard to the weight and identity of the recipient.

While it is possible for the compounds to be administered as the raw chemical, it is preferably to present them as a pharmaceutical formulation preparation. The formulations, for human or for veterinary use, comprise a compound of formula (I) as above defined, together with one or more acceptable carriers therefor and optionally other therapeutic ingredients. The carrier(s) must be 'acceptable' in the sense of being compatible with the other ingredients of the formulation and not deleterious to the recipient thereof.

The formulations include those suitable for oral, parenteral (including subcutaneous, intradermal, intramuscular and intravenous) and rectal administration although the most suitable route may depend upon for example the condition and identity of the recipient. The formulations may conveniently be presented in unit dosage form and may be prepared by any of the methods well known in the art of pharmacy. All methods include the step of bringing into association the compound of formula (I) (the active ingredient) with the carrier which constitutes one or more accessory ingredients. In general the formulations are prepared by uniformaly and intimately bringing into association the active ingredient with liquid carriers or finely divided solid carriers or both, and then, if necessary, shaping the product into the desired formulation.

Preferred unit dosage formulations are those containing a daily dose or unit daily sub-dose, as hereinabove recited, or an appropriate fraction thereof, of a compound of formula (I).

A further application for the compounds of formula (I) is the extracorpreal treatment of blood from the (generally human) patient. As one possibility such treatment may be conducted in a batch-wise manner by removing an appropriate volume of blood, admixing it with the compound and transfusing the treated blood back into the patient. As an alternative possibility the treatment may be on a continuous basis, analogous to the well-known techniques for haemodialysis, whereby for a period of time blood is continuously withdrawn, admixed with the compound and passed back into the patient. Both procedures should be conducted under sterile conditions and may be repeated as often as necessary. An effective blood concentration of a compound of formula (I) will generally be in the range 0.1 mM to 50 mM, more generally in the range 0.5 mM to 25 mM and most often in the range 1 mM to 10 mM, with an optimum concentration of 3 mM.

For in vitro use in the storage of red blood cells as previously described the compounds are conveniently admixed with the cells in the vessel in which the latter are collected and stored; this conventionally takes the form of a bottle or bag of sufficient size to hold the customary whole blood unit (circa 450 ml.) together with an aliquot of anticoagulant. A compound may be brought into contact with the cells at any appropriate point between their collection from the donor and their transfusion (together with the compound) into the recipient. As one possibility therefore the compound, in association with the anticoagulant, is present within the bottle or bag when the latter is "ready for use", the admixture occurring upon entry of the blood, while in an alternative approach the compound is added to cells already held within the bottle/bag, for example immediately subsequent to collection or just prior to use (transfusion). The compounds may be used in this fashion whether the cells are stored in the form of whole blood or as a packed cell mass (when the plasma is held separately) and, in the latter case, whether transfused resuspended in plasma or in a plasma substitute.

The effective concentration of a compound, in whole blood volume in a bottle or bag as above described, will generally be in the range 0.1 mM to 50 mM, more generally in the range 0.5 mM to 25 mM and most often in the range 1 mM to 10 mM, with an optimum concentration of 3 mM. Although the precise weight of compound required will vary with its identity a standard size bottle/bag (vide supra) will require circa 0.5 g (calculated as the acid) to provide the optimum 3 mM concentration.

The following Examples are provided in illustration of the present invention and should not be construed as in any way constituting a limitation thereof. All temperatures are in degrees Celsius.

EXAMPLE 1

Activity in whole human blood in vitro

Human blood was collected from volunteer donors into CPD anticoagulant* medium in the ratio 100 ml blood:15 ml medium; 1 ml aliquots were dispensed into 2 ml polycarbonate vials and then kept for three hours at 4° C. to allow the cells to settle out from the plasma. The samples were then held at room temperature while the test compounds, one per vial, were added according to the following procedure to provide a 6 mM concentration in whole blood volume:

A small volume of plasma was removed from each vial: sodium salts (q.v.) were dissolved therein directly while acids (q.v.) were added to warm aqueous sodium bicarbonate (300 mM, 2 drops) which was then mixed with the plasma; in either case the compound-laden plasma was then returned to the original vial, the vial capped and the contents mixed thoroughly.

*CPD anticoagulant is an aqueous solution containing the following per 100 ml:

| | |
|---|---|
| Sodium citrate | 2.63 g |
| Anhydrous dextrose | 2.32 g |
| Citric acid monohydrate | 0.327 g |
| Sodium acid phosphate | 0.251 g |

For each experimental series three control vials were also prepared containing respectively:
(a) blood alone
(b) blood + hydrochloric acid (0.1M, 150 microliter)
(c) blood + aqueous sodium hydroxide (0.1M, 150 microliter).

After a total of two hours at room temperature all samples were left at 37° C. for 16 hours and the pH of each then measured at that temperature. The vials were then stored on ice and the oxygen-dissociation curve determined for each sample using a whole-blood spectrophotometer (Hem-O-Scan, Trade Name). Finally, after rewarming to 37° C., the pH of each sample was remeasured.

The right-displacement of the $P_{50}$ point (the oxygen tension at which the haemoglobin is 50% saturated with oxygen) for the oxygen-dissociation curve was ascertained for each sample relative to the calculated $P_{50}$ value for the appropriate sample pH. The results are given below.

| Compound Formula (I) | Right displacement (mm Hg) |
|---|---|
| 3'-Hydroxy | 13.1 |
| 3'-Methoxy | 12.5 |
| 3'-(2-Hydroxyethoxy) | 6.0 |
| 4'-Hydroxy | 11.8 |
| 4'-(2-Hydroxyethoxy) | 9.6 |

EXAMPLE 2

Pharmaceutical Formulations

| (A) CAPSULE | |
|---|---|
| Compound (acid) | 625 mg |
| Starch 1500 | 250 mg |
| Magnesium stearate | 8 mg |
| | 883 mg |

Mix the ingredients using a suitable mixer and fill into capsules on a capsule filling machine.

| (B) TABLET | |
|---|---|
| Compound (acid) | 625 mg |
| Lactose | 200 mg |
| Polyvinylpyrrolidone | 50 mg |
| Starch | 100 mg |
| Magnesium stearate | 10 mg |

| (B) TABLET |        |
|------------|--------|
|            | 985 mg |

Dissolve the polyvinylpyrrolidone in a suitable volume of water. Mix the compound, lactose and starch and add the polyvinylpyrrolidone solution. Add a further quantity of water if required. Pass through a suitable screen and dry. Add the magnesium stearate, mix and compress on a tabletting machine.

| (C) SUPPOSITORY |        |
|-----------------|--------|
| Compound sodium salt, equivalent to acid | 1.25 g |
| Hard fat B.P. to | 3 ml |

Melt part of the hard fat at 50° C. maximum. Add the compound to the molten base and disperse. Add the remaining hard fat to the suspension. When a smooth homogenous suspension has been obtained pour the suspension into 3 ml moulds.

| (D) INJECTION |           |
|---------------|-----------|
| Compound sodium salt, equivalent to acid | 1.25 g |
| Mannitol B.P. | 125.0 mg |
| Water for injections BP/Ph/Gm to | 2.5 ml |

Dissolve the compound and the mannitol in ⅔ the final quantity of water for injections. Make the volume with more water for injections. Sterilise the solution by passage through a sterilising grade filter. Fill 2.5 ml portions into suitable vials under aseptic conditions and freeze dry. When drying is complete seal the vials under an atmosphere of oxygen free nitrogen and cap with aluminium collars.

| (E) INJECTION |          |
|---------------|----------|
| Compound (acid) | 2.50 g |
| Benzyl alcohol | 90.0 mg |
| TRIS solution (0.05 M) | 5 ml |
| Hydrochloric acid (0.1 N) | 3 ml |
| Water for injections BP/Ph/Gm to | 10 ml |

Dissolve the compound in the TRIS and hydrochloric acid. Add and dissolve the benzyl alcohol and make to volume with water for injections. Sterilise the solution by filtration through a suitable sterilising grade filter. Fill into 10 ml vials under aseptic conditions and seal with rubber closures.

In the foregoing, (acid) indicates that the compound (of formula (I)) is present as the free carboxyl acid.

EXAMPLE 3

Blood Storage

A sterile, sealed bag (Fenwal, Travenol Laboratories Ltd., Thetford, Norfolk, England) suitable for collection of 420 ml blood and containing 63 ml of CPD anticoagulant solution, was taken. Under sterile conditions the anticoagulant was removed, admixed with an effective, non-toxic amount (vide supra) of a compound of formula (I) and returned to the bag and the bag then resealed and stored at room temperature.

Blood from a volunteer human donor was subsequently collected into the bag by conventional procedures and the full bag then stored at 4°–6° C.

We claim:

1. A method for increasing the delivery of oxygen to the tissues of a mammal in need of an increased amount of oxygen to its tissues comprising administering to said mammal in need thereof a non-toxic, oxygen delivery increasing amount of a compound of formula (I)

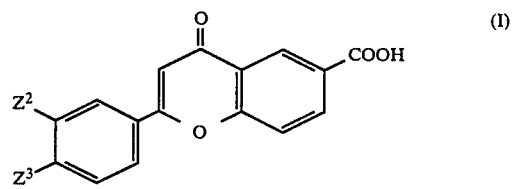

wherein
one of $Z^2$ and $Z^3$ is selected from the group consisting of hydroxyl and a group $-O(C_nH_{2n})X$
where
X is selected from the group consisting of hydrogen and hydroxyl and
n is an integer from 1 to 3
provided that when X is hydroxyl then n is always greater than 1 and no single carbon atom in the radical $-(C_nH_{2n})-$ is attached to both oxygen atoms and
the other of $Z^2$ and $Z^3$ is hydrogen,
or a pharmacologically acceptable salt thereof.

2. The method of claim 1 in which 3'-methoxyflavone-6-carboxylic acid or a pharmacologically acceptable salt thereof is administered.

3. The method of claim 1 in which the compound or salt thereof is administered with an acceptable carrier therefor.

4. The method of claim 2 in which the compound or salt thereof is administered with an acceptable carrier therefor.

5. The method of claim 1 in which the mammal is a human being.

6. The method of claim 2 in which the mammal is a human being.

7. A method for the relief of tissue hypoxia in a mammal suffering from tissue hypoxia comprising administering to said mammal suffering from tissue hypoxia and in need thereof a non-toxic, tissue hypoxia relieving amount of a compound of formula (I)

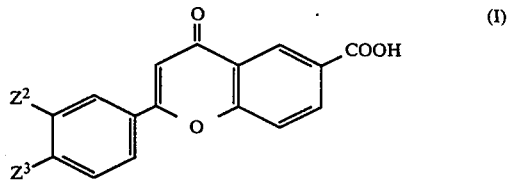

wherein
one of $Z^2$ and $Z^3$ is selected from the group consisting of hydroxyl and a group $-O(C_nH_{2n})X$
where
X is selected from the group consisting of hydrogen and hydroxyl and
n is an integer from 1 to 3,
provided that when X is hydroxyl then n is always greater than 1 and no single carbon atom in the radical —$(C_nH_{2n})$— is attached to both oxygen atoms and the other of $Z^2$ and $Z^3$ is hydrogen, or a pharmacologically acceptable salt thereof.

8. The method of claim 7 in which 3'-methoxyflavone-6-carboxylic acid or a pharmacologically acceptable salt thereof is administered.

9. The method of claim 7 in which the compound or salt thereof is administered with an acceptable carrier thereof.

10. The method of claim 8 in which the compound or salt thereof is administered with an acceptable carrier therefor.

11. The method of claim 7 in which the mammal is a human being.

12. The method of claim 8 in which the mammal is a human being.

* * * * *